(12) United States Patent
Phelan et al.

(10) Patent No.: US 7,537,577 B2
(45) Date of Patent: *May 26, 2009

(54) LOW-PROFILE, RADIAL NERVE SPLINT WITH INTERCHANGEABLE RESILIENT DIGIT EXTENSOR ELEMENTS AND SUPINATION ADJUSTMENT MEANS

(76) Inventors: Carolyn Hoyne Phelan, 6180 Rancho Diegueno, Del Mar, CA (US) 92014; Daniel Robert Baumgartner, 11871 Silverdale Way NW. #107, Silverdale, WA (US) 98383; Timothy John Baumgartner, 7701 Rita Rd. NE., Bremerton, WA (US) 98311

( * ) Notice: Subject to any disclaimer, the term of this patent is extended or adjusted under 35 U.S.C. 154(b) by 0 days.

This patent is subject to a terminal disclaimer.

(21) Appl. No.: 11/480,645

(22) Filed: Jul. 5, 2006

(65) Prior Publication Data

US 2006/0276735 A1 Dec. 7, 2006

Related U.S. Application Data

(63) Continuation-in-part of application No. 11/145,777, filed on Jun. 6, 2005.

(60) Provisional application No. 60/641,205, filed on Jan. 3, 2005.

(51) Int. Cl.
*A61F 5/00* (2006.01)
*A63B 23/14* (2006.01)
*A63B 23/16* (2006.01)
*A41D 19/00* (2006.01)
*A61F 5/37* (2006.01)

(52) U.S. Cl. .................... 602/21; 602/5; 602/9; 602/12; 128/878; 128/879; 482/44; 2/159

(58) Field of Classification Search ................ 602/5–6, 602/12, 20–22, 62, 64, 9; 128/878, 880; 482/44, 47–48; 2/159, 160, 161, 161.1, 161.2, 2/161.6, 161.7, 162, 163
See application file for complete search history.

(56) References Cited

U.S. PATENT DOCUMENTS

| 859,097 | A | * | 7/1907 | Miller | ........................ 2/161.8 |
| 2,108,236 | A | * | 2/1938 | Scott | ........................... 482/48 |
| 4,103,682 | A | * | 8/1978 | Franzl | ....................... 602/22 |
| 4,366,812 | A | * | 1/1983 | Nuzzo | ......................... 602/22 |
| 4,781,178 | A | * | 11/1988 | Gordon | ...................... 602/22 |
| 5,282,483 | A | * | 2/1994 | Wang | ......................... 128/882 |

(Continued)

*Primary Examiner*—Patricia M Bianco
*Assistant Examiner*—Brandon Jackson
(74) *Attorney, Agent, or Firm*—Eric Hanscom; Todd Langford

(57) ABSTRACT

A low-profile, simple, orthotic glove with wrist support attachment for treating loss or impairment of extensor and/or flexor muscle function in the upper extremities, particularly in the wrist, hand and fingers, due to a peripheral neuropathy. The glove is attractive, comfortable, easy to use, and can be made with an optional wrist support attachment either built into the glove or added as an optional attachment, and can include thermoplastic to provide rigidity. The glove has channels into which interchangeable resilient digit extensor elements, or stays, of varying resiliency are placed such that stays of greater or lesser resiliency can be inserted if the degree of the patient's extensor muscle control changes, or the medical practitioner in charge decides that there is a need to change the support and exercise treatment regimens. The splint also has several improvements for thumb support, additional digit extension support, and for supination of the forearm.

18 Claims, 9 Drawing Sheets

U.S. PATENT DOCUMENTS

| | | | |
|---|---|---|---|
| 5,453,064 A * | 9/1995 | Williams, Jr. | 482/47 |
| 5,697,103 A * | 12/1997 | Wiggins | 2/159 |
| 5,921,945 A * | 7/1999 | Gray | 602/5 |
| 6,216,276 B1 * | 4/2001 | Eibert | 2/161.2 |
| 6,557,177 B2 * | 5/2003 | Hochmuth | 2/159 |
| 6,561,995 B1 * | 5/2003 | Thibodo, Jr. | 602/22 |
| 7,135,006 B1 * | 11/2006 | Weber et al. | 602/22 |

* cited by examiner

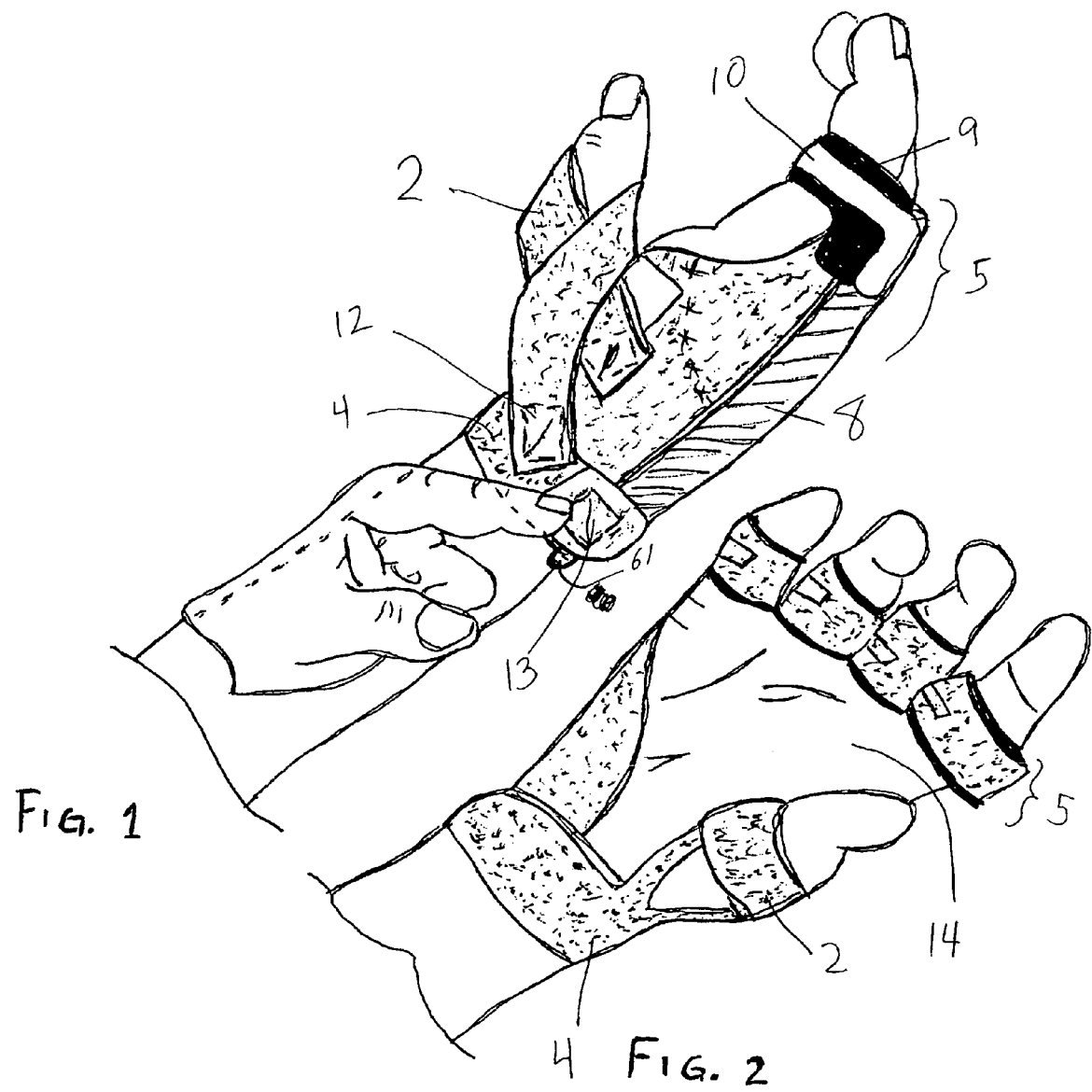

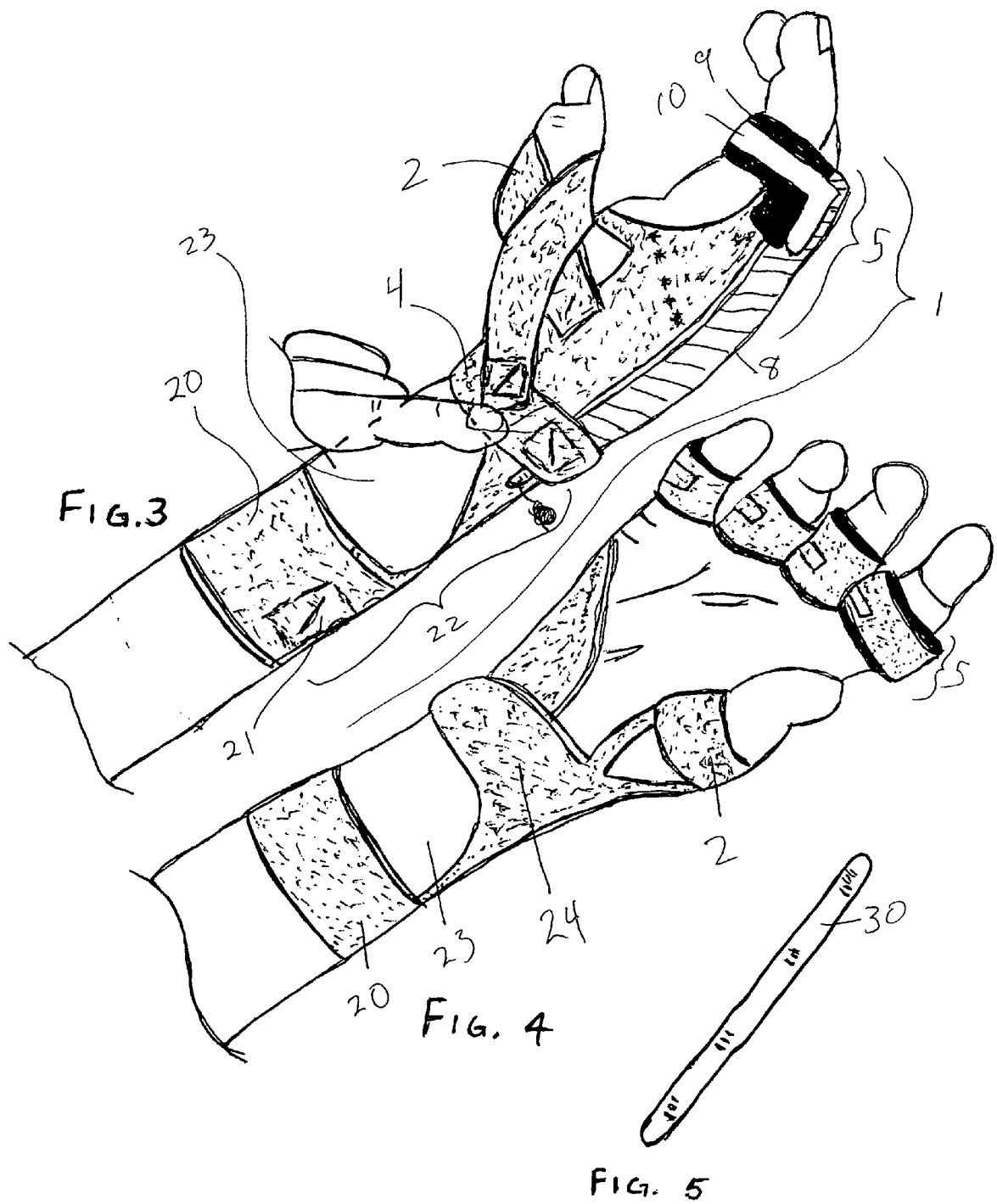

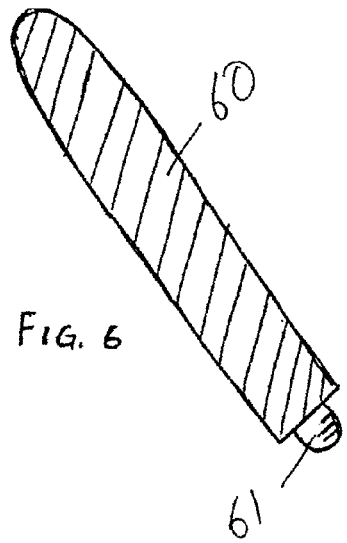
FIG. 6
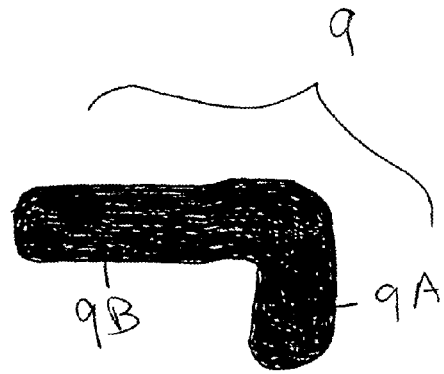
FIG. 7
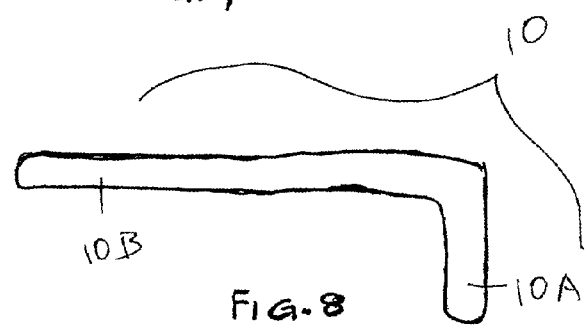
FIG. 8
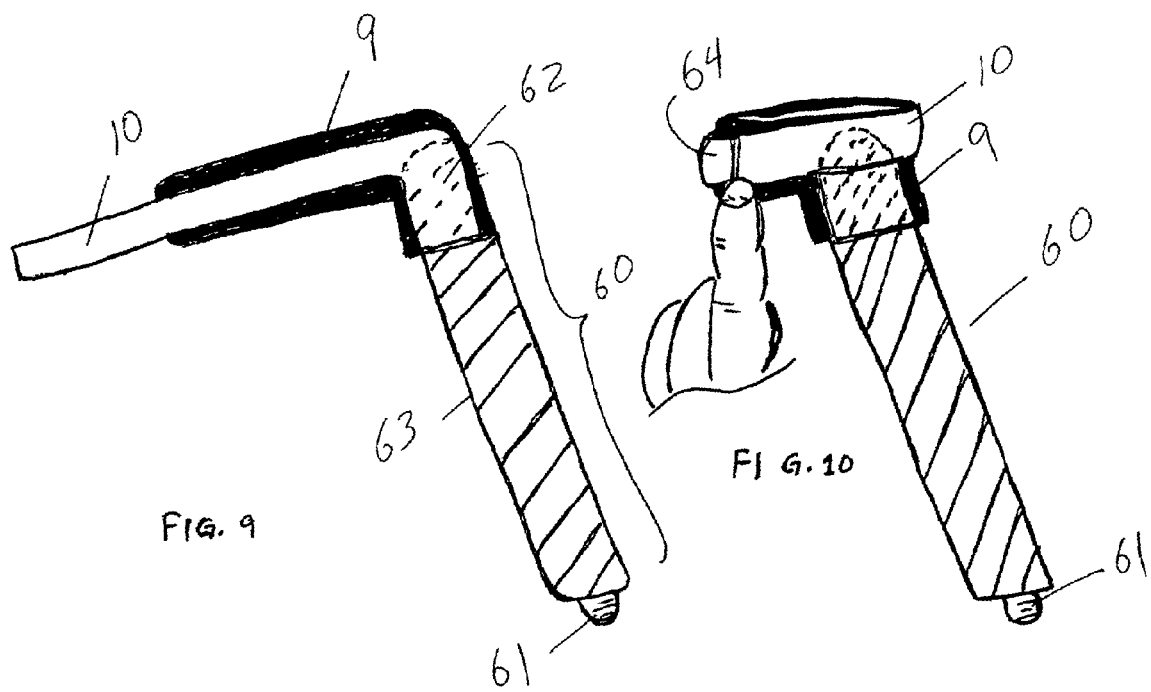
FIG. 9
FIG. 10

LOW-PROFILE, RADIAL NERVE SPLINT WITH INTERCHANGEABLE RESILIENT DIGIT EXTENSOR ELEMENTS AND SUPINATION ADJUSTMENT MEANS

CROSS REFERENCE TO RELATED APPLICATIONS

This is a continuation-in-part of application Ser. No. 11/145,777 filed on Jun. 6, 2005, which is a continuation of application No. 60/641,205 Jan. 3, 2005, the entireties of which is incorporated by reference.

STATEMENT REGARDING FEDERALLY SPONSORED RESEARCH OR DEVELOPMENT

This invention was not federally sponsored.

FIELD OF THE INVENTION

This invention relates to medical devices that compensate for functional losses in patient mobility, particularly losses associated with radial or peripheral nerve injuries. More specifically, this invention is directed toward a low-profile, simple, orthotic glove with wrist support attachment for treating loss or impairment of extensor and/or flexor muscle function in the upper extremities, particularly in the wrist, hand and fingers, due to a peripheral neuropathy. The glove is attractive, comfortable, easy to use and adjusts to different injuries and medical/treatment needs, inexpensive to produce, and provides alternatives for wrist support. The glove has channels into which interchangeable resilient digit extensor elements, or stays, of varying resiliency are placed such that stays of greater or lesser resiliency can be inserted if the degree of the patient's extensor muscle control changes, or the medical practitioner in charge decides that there is a need to change the support and exercise treatment regimens.

BACKGROUND OF THE INVENTION

Medical splints have been widely used for many centuries in treating a wide range of medical disorders. There exist several prehistoric skeletons which show broken limbs which had been properly set with splints such that the owner of the limb was able to live a decade or so after breaking the bone before he/she died. The earliest written and pictorial records of splints come from ancient Egypt, where splints were made from reeds, bamboo, and bark padded with linen, and used primarily for treating fractures. The next recorded innovation in splints and splinting technique occurred around 1500 BC when copper splints were used to treat burns. Around 460 BC, no less than the famous Greek medical giant Hippocrates invented, or perhaps was the first to write about, the use of leather straps to hold splints on a fracture. Indeed, Hippocrates' leather straps were the state of the art until relatively recently, when plastic was invented. In North and South America, the historical record of medicinal advancements is sparse compared with the great written histories of Egypt, Greece and Rome, but it is well documented that the use of splints to treat broken bones was a well known and advanced art in many parts of the pre-Columbian Americas at the time of initial contact with Europeans.

During the 1900's, in addition to the discovery of plastic and its multitudinous variety of uses, the medical fight against polio and the necessity of splinting a variety of injuries under less than idea battlefield conditions during the two world wars led to rapid advancement in splinting technology. Today, splints are used to deal with an incredibly wide range of medical problems and disorders, a far cry from the splint's initial use for broken bones. Indeed, splinting has its own classification system and medically-directed standards can be found for treating different situations.

One situation in which splints are used for purposes other than mending broken bones is in the treatment of peripheral neuropathies, a term which encompasses problems with the nerves outside of the brain and spinal cord, specifically the arms and legs. For example, one well known peripheral neuropathy is Guillain-Barre' syndrome, a disease having an incidence rate of approximately 1.7 cases per 100,000 annually, which arises from complications associated with viral illnesses, such as those caused by cytomegalovirus (CMV). Epstein-Barr virus (EBV), and human immunodeficiency virus (HIV), or bacterial infection, including those caused by campylobacter jejuni and Borrelia burgdorferi (Lyme disease).

Other causes of peripheral neuropathies include chronic alcoholism, infection by the varicella-zoster virus, botulism, and poliomyelitis. Peripheral neuropathy may develop as a primary symptom, or it may be due to another disease. For example, peripheral neuropathy is only one symptom of diseases such as amyloid neuropathy, certain cancers, and some inherited neurological disorders. Such diseases may affect the peripheral nervous system (PNS) and the central nervous system (CNS), as well as other body tissues. Peripheral neuropathy may involve damage to a single nerve or nerve group (mononeuropathy) or may involve multiple nerves (polyneuropathy).

Before WWII, nerves were believed to be cords and consequently received little attention. Nerve repair consisted of simple reapproximation and suturing. During WW I, nerve injuries were repaired under tension and risked disruption after repair because of extensive soft tissue injuries and significant infections. During WW II, reoccurrence of these war injuries influenced experimental studies to further investigate the anatomy of the peripheral nerve. Poor outcomes of peripheral nerve damage repair were recognized to be the result of failed axonal regeneration at the site of the repair (Colohan, 1996). An important quality of the peripheral nervous system, as compared to the central nervous system, is its remarkable ability to recover after an injury through remyelination and regeneration of the axon (Grant, 1999).

Nerves can also be affected by injury from mechanical, thermal, chemical or compression means, causing ischemia. The prognosis for recovery from these peripheral nerve injuries depends upon which structures of the nerve were damaged i.e., axon, endoneurium, perineurim, epineurium) and how much of the nerve was damaged. (Malick, 1984; Kasch, 1984)

Classification of nerve injury is based on damage sustained by the nerve components, nerve functionality, and the ability for spontaneous recovery (Grant, 1999; Greenfield, 1997; Ristic, 2000). Seddon (1943) published his three classification of nerve injuries, and Sunderland (1951) expanded his grading system to five (Ristic, 2000).

Neuropathy involves damage to the axon of the nerve cells wherein degeneration of the axon or its surrounding myelin sheath slows or blocks nerve signal conduction at the point of the degeneration. Demyelination (destruction of the myelin sheath around the nerve cell) greatly decreases the speed of impulse conduction through the nerve. Injury mechanisms can include mechanical injury, compartment syndromes, trauma to peripheral nerves, fractures, stretch injuries and neuropathies. Neuropathies can also be caused by the effects of age, an autoimmune disorder, and other chronic diseases, including multiple sclerosis. Neuropathies can further arise due to acute injury to the nerves, such as by severing or blunt force trauma, as can occur in laceration and compression injuries.

The result of damage to the nerve fibers includes the impairment of voluntary movement or function of the area of muscle controlled by the nerve because impulses to the area are blocked. Impaired nerve stimulation to a muscle can result in weakness, decreased movement, loss of control of movement, etc. These effects, in turn, can lead to structural changes in muscle, bone, skin, hair, nails, and body organs due to reduced use of the affected area, immobility, lack of weight bearing, etc. For example, nerve injury can result in muscle weakness, atrophy, and loss of muscle mass. Injury also often results in the loss of sensation and control of the muscles served by the damaged nerves. Such damage can also give rise to infection or structural damage. Changes may include ulcer formation, poor healing, loss of tissue mass, scaring, and deformity. No matter what the cause or type of the neuropathy, the resulting situation is that due to damage to the nerve, a certain part of the body either no longer functions or functions with lesser ability than it originally functioned. The current invention serves to treat these types of problems in a unique and functional manner.

Neuropathies can be either permanent or treatable. Treatment is possible primarily because in some cases where immediate repair or re-growth is not possible, other nerves lying near to those that have been damaged may branch out and connect to the muscles that were previously served by the damaged nerves. The prognosis and speed of peripheral nerve recovery are directly dependent upon such factors as the level and severity of injury, surgical intervention, and the subsequent rehabilitative process. Severe injuries may take months or years for the affected peripheral nerve(s) to recover, if ever. In many cases, it is at least beneficial and in some cases essential that these nerve and muscle group be partially or fully immobilized, or positioned such that they can function with less stress put on the injured part of the body.

In neuropathies affecting muscles of the wrist, hand and fingers, prolonged muscle imbalance due to loss of muscle control can result in joint contractures and over-stretching or extension of denervated muscles. Without proper care, wrist and/or hand function recovery may be limited or may not occur at all. Though the recovery of muscle strength may occur, the loss of sensation (for example, to temperature, pain, or pressure) may not.

The principles behind splinting and caring for a neuropathy are simple and straightforward:

5. Protect denervated muscles from being overstretched. Muscles generally work in a competitive tandem, where one set of muscles plays against another set in moving an appendage one way or the other. When one set of the muscles is weakened due to injury or lack or impairment of neural function, the "innervated" set of muscles can easily overpower and overstretch the weakened or impaired muscles, potentially resulting in further injury and delayed or even reduced recovery possibilities.

6. Prevent undesirable substitution patterns and establish normal hand functions. Without a splint, a patient may adapt to the imbalance and try to maintain the previously easy hand motions by using new and anatomically damaging methods.

7. Prevent joint contractures. Should a patient be allowed to substitute the aforementioned undesirable hand patterns to compensate for the loss of normal hand motion, it is highly likely that the joint will develop a contracture from being taken through less than its full range of motion.

8. Encourage patient compliance. Even the greatest medical strategies for treating peripheral nerve damage will prove useless if the patient doesn't use the splint. Among the important factors in whether a patient will actually use the splint outside of the medical practitioner's line of sight include the attractiveness and appearance of the splint, along with its comfort and ease of use. For example, a number of studies, including Hannah/Hudak (2001), Alsancak (2001) and Ven Lede (2002), show that the most important factor in whether splint compliance was adhered to by patients was aesthetic appearance, with lower profile, functional use, and less structure also being important factors.

Use of a splint is typically employed during the nerve regeneration period of recovery. Splinting helps to minimize the occurrence of deforming joint contractures caused either by hyper-flexing or by hyper-extension of the muscle groups in the affected muscles. Proper splinting also encourages safe and protected use of the injured hand in daily activities. This is true particularly when dealing with wrist and hand injuries, as peripheral neuropathies relating to the wrist and hand frequently require protected regular exercise to have a reasonable chance of partial or total recovery. Thus, there has existed a need for a functional splint that allows for this protected exercise and movement of the wrist/hand with patients who have suffered a peripheral neuropathy.

The invention is particularly directed toward treating patients with radial nerve peripheral nerve damage which allows them to flex their wrist but not extend it, and to flex their fingers but not extend them, a condition generally known as radial nerve palsy. With this condition, a patient whose hand is open can, for example, grasp a can to pick it up, but cannot unclasp his/her fingers or thumb from the can to release it. The invention allows the patient to unclasp his/her fingers from the can, place the can in its desired location, and then be ready to close the hand on another object, as the stays pull the fingers and thumb back into their original, open position. Using the glove also provides wrist support, which is needed to correctly position the patient's wrist for proper usage of the fingers.

In trying to come up with a splint which will assist patients with peripheral and radial nerve damage, it cannot be understated how important the appearance of the splint is in terms of whether the patient will actually use it. A number of studies show that the most important factor in whether a patient will use a particular splint is not how well it works or how comfortable it is, but rather, how it looks. While many in the medical field may find this fact to be disappointing, it remains a fact that cannot be discounted when assessing whether a particular product will help the patient—the best splint in the world is useless if the patient does not use it. As will be seen from some of the prior art, many of the previous attempts to treat peripheral nerve damage were highly expensive and obtrusive machines with many metal wires, springs and clamps which looked more appropriate in a horror movie than on a person. Thus, it is easy to see why many examples of the prior art were not worn substantially outside of the medical practitioner's office.

The prior art has several examples of attempts to resolve this problem. Splints are obviously well know to the medical arts, having been used centuries before the first patent office was formed. The prior art also provides numerous examples of current splints for supporting or treating nerve damage-based injury to voluntary muscle mobility of the hand and digits include supports and splints for use on the hand and digits, however none of these provides a device which can treat a peripheral neurological injury to the hands and/or fingers which is both functional and attractive, comfortable, and user-friendly—in short, a splint that a patient is likely to wear. The prior art also lacks a splint which is adaptable to a range of different sized hands, is relatively inexpensive to produce, and allows the medical practitioner a wide degree of flexibility in treating the neuropathy.

The prior art includes a number of splints which allow for retention and/or strengthening of the fingers. General purpose hand splints, such as those illustrated by U.S. Pat. Nos. 3,938,509 to Barber and 5,466,202 to Stern show the range of splints—from aluminum/foam to inflatable vinyl sheets. These splints, however, do not allow for the selective treatment of peripheral and radial nerve damage as does the current invention. Some, such as U.S. Pat. No. 6,093,162 to Farleigh and U.S. Pat. No. 4,619,250 to Hasegawa, are so unwieldy as to be suitable solely for a medical office, as they require such complex machinery to work that they could not be used at a patient's home or while a patient was walking, driving, or performing other normal daily activities. A number of exercising splints, such as U.S. Pat. Nos. 5,113,849 to Kulken, 6,547,752 B2 to Holland, and 6,059,694 to Villepigue, teach devices used to exercise some combination of the fingers, hand, and thumb muscles and nerves. These patents, however, are unwieldy and are useful mainly for exercising, as opposed to the current invention whose uniqueness comes in large part from its ability to be worn throughout the day and to assist the user in not only exercising and improving the damaged nerves and recovering muscles, but also allowing the user to perform daily functions such as picking up a glass of water to drink, that would be otherwise impossible for the user of the invention to accomplish due to his/her neuropathy. There are also splints which serve to retain or partially retain and immobilize the user's fingers, as seen in U.S. Pat. Nos. 5,921,945 to Gray, and 5,766,142 to Hess. These splints, however, serve only to restrain the fingers rather than encouraging the damaged nerves and muscles to heal, and neither of these splints would allow for a user to clasp and unclasp his/her hand in performing normal hand functions.

There are also a number of unpatented splints on the market today which attempt to address the need for comfortable and functional splint that can be used effectively to treat patients with peripheral nerve damage. For example, there are a number of splints by Oppenheimer and Thomas which use a combination of attachment mechanisms, springs, and wires which provide a patient with a means to unbend the fingers and thumbs after the patient has bent them. These devices, however, as the pictures in their advertisements will make readily apparent, have a large number of delicate springs and wires extending up, out, down and to the side from the patient's wrist and hand up to several inches, thereby both increasing the danger that the splint will be damaged during normal use and restricting the potential uses the patient can make of his/her hand while wearing such a device. These splints are also extremely unattractive, thereby severely decreasing the likelihood that they will be used regularly by the patient.

Finally, the prior art also has several examples of glove-type splints. U.S. Pat. No. 5,014,689 to Meunchen teaches a hand brace with dorsal and palmar hand sections which attach to one another forming a fingerless glove which serves to support the wrist and hand to prevent, reduce, or control carpal tunnel syndrome. This patent does not, however, teach any type of device which relates to the fingers of the hand. Another patent relating to gloves is U.S. Pat. No. 6,010,473 to Robinson. This glove is used by an individual with nerve damage which has hampered the use of the hand, and serves to hold one or more fingers in a set, desired position, with a stated purpose of "provid[ing] comfort to the user while also serving to lessen the obviousness of any hand or finger grotesqueness." As such, the Robinson patent does not supply a means by which a person with nerve damage to his/her hand can use a glove-like device to improve the functioning of his/her hand.

Commercially available glove-type splints include the Robinson Peripheral Nerve Splint, currently sold by AliMed Inc., is a set of two items, where the inner item is a strip of plastic running over the patient's dorsal hand, from which five "InRigger springs" project, one each to lie dorsally over each finger and the thumb. The "InRigger springs" are metal strips that are resilient enough to "pull" a finger back up after it has been flexed forward. Over this device is fitted a glove, which serves to pull the fingers back up when the metal strips exert their pull. While the Robinson splint avoids the unwieldy and unattractive springs and wires of the Oppenheimer and Thomas splints, it does not provide a complete solution to the problem of providing a simple yet effective method of allowing for flexibility in the treatment of peripheral neuropathies. Since each "InRigger" spring is made with a pre-set tensile strength, there is no adjustability possible. It is also fairly cumbersome to use, as the user first has to align the inner part and then pull over the glove portion, an activity not easy for someone with limited, at best, use of one hand. Finally, although more attractive than the Frankensteinesque Oppenheimer and Thomas splints, the Robinson splint still looks like an overstuffed gardening glove, again, a "look" not likely to cause many patients to use it.

Thus, although the medical field has a number of splints and supports that have been used for treatment of radial nerve damaged muscles, the field still lacks effective splints that have a user friendly, esthetically pleasing low-profile that, at the same time, provide for versatile, life-like operation and allow for easy interchangeability of the components that compensate for muscular and nerve deficits. Thus there has existed a long-felt need for an attractive, comfortable, and user-friendly means of splinting and treating a peripheral neurological injury to the hands and/or fingers. The need extends to a splint which the user is likely to wear, which allows the medical practitioner a wide degree of flexibility in treating the neuropathy, which is adaptable to a range of different sized hands, and is relatively inexpensive to produce.

The current invention provides just such a solution by having a low-profile, simple, orthotic glove with wrist support attachment for treating loss or impairment of extensor and/or flexor muscle function in the upper extremities, particularly in the hands and fingers, due to a peripheral neuropathy. The glove is attractive, comfortable, easy to use, inexpensive to produce, and can be made in versions with or without a wrist support attachment either built into the glove or added as an optional attachment, and can include thermoplastic to provide rigidity. The glove has channels or tunnels into which interchangeable resilient digit extensor elements, or stays, of varying resiliency are placed such that stays of greater or lesser resiliency can be inserted if the degree of the patient's extensor muscle control changes, or the medical practitioner in charge decides that there is a need to change the support and exercise treatment regimens. The splint also has several improvements for thumb support and for supination of the forearm.

SUMMARY OF THE INVENTION

It is a principal object of the invention to provide a glove which can be used to treat peripheral nerve damage in the upper extremities.

It is another object of the invention that the glove be attractive, easy to attach and detach, and can be worn during many daily activities such that a patient is likely to use the glove outside of the medical practitioner's office.

An additional object of the invention is that the glove can be manufactured in to cover all the patient's fingers and thumbs, be open on one or more fingers or thumb, have removable sections which would cover one or more fingers or thumb, be full fingered, cover only the first or second knuckle of the finger, or expose the entire finger or thumb.

It is an additional object of the invention that the glove have an optional wrist support which can be used according to the comfort of the user and the direction of the supervising medical practitioner, where the wrist support can be attached to the glove through a variety of means including snaps, zippers, hook and loop fastener, threaded string or similar devices.

An additional object of the invention is that the glove includes a flexible, comfortable thumb strap that keeps the thumb properly positioned.

It is also an object of this invention that the glove be adjustable to a patient's hand, where such adjustability can come from one or more of the following means: the natural elasticity of the glove material, adjustable straps, adjustable zippers, adjustable snaps, hook and loop fastener, threaded string or similar devices.

It is a further object of the invention that the glove function by keeping the patient's hand in an "open" position, such that the functional flexor muscles can close the hand to grasp objects and perform many daily, routine activities, and that the glove will then push the fingers and thumb of the hand back into the "open" position once the grasping action is no longer desired, as, for example, when a user has grasped a can, moved it to a new location, released the can, and is now ready to pick up something else.

It is another object of the invention that the glove have no outriggers, loops, wires, or other projections sticking out of it which could cause the glove to be difficult to use or unattractive to the patient.

It is an additional object of the invention that the glove allows for use by patients with less than a 25 pound grip.

It is a further object of the invention that the glove has at least one tunnel or channel in its upper surface into which one or more stays can be inserted to provide the resiliency necessary to return a finger or thumb to its "open" position after it has been closed.

An additional object of the invention is that the stays are interchangeable, such that one stay can be substituted for another easily and quickly.

It is a further objection of the invention that the tunnel or channel into which the stay is inserted can have an opening in the middle such that the stay is compressed slightly and the ends slipped into the tunnel openings before the stay is allowed to uncompress, or at either end such that the stay is slid into the tunnel and then a cover is attached over the end of the stay, securing the stay in the tunnel.

It is also an object of this invention that the stays be made in a planer, rectangular, angular, circular, hollow tube like, or multi-parted fashion.

It is a further object of the invention that the stay can be uniformly thick or tapered such that it is thicker at one end than the other.

An additional object of the invention is that the stay can be manufactured with a uniform resiliency throughout or with varying resiliency such that, for example, it has greater resiliency toward the hand and lesser resiliency at the finger portion of the glove.

It is an additional object of the invention that the stays can be manufactured with different degrees of resiliency such that stays of different resiliencies can be interchangeably inserted into the glove depending on the patient's progress and prescribed treatment regimen.

A further object of this invention is that the stays can be made of adjustable resiliency such that a stay can be adjusted over time as the patient's progress and treatment plan changes.

It is also an object of this invention that the glove be inexpensive to manufacture, and can be manufactured in a variety of sizes to accommodate different sizes of hands, wrists, and fingers.

It is another object of the invention that the glove can be manufactured from a wide variety of materials, including plastic, leather, Lycra, polyester, imitation leather, neoprene, compression garment material, and hypoallergenic materials, or perhaps breathable materials to avoid the accumulation of moisture on the palmar surface.

A further object of the invention to provide a glove which can be made with a one-piece hard shell which extends from the mid-digital area to the dorsal forearm, such that the glove provides wrist support.

An additional object of the invention provides versatility with respect to how many tunnels and stays can be used.

Further objects of the invention include providing a variety of ways in which the tunnels or channels can be attached to the glove, including having them sewn or glued to the glove, and having them detachable and adjustable by way of hook and loop fastener or other removable and adjustable methods.

Another object of the invention is to provide an adjustable and removable digit splint that can be used for either a finger or a thumb.

A further object of the invention is to provide for the use of thermoplastic as the material from which the support section of the glove is made, such that a user of the invention has the ability to heat the thermoplastic to modify the glove to conform to his/her individual hand and wrist.

Additional objects of the invention include providing a glove which has a supination strap which is attachable to the glove.

Another object of the invention is to provide a digit extension strap, which is optionally attachable to the glove.

It is a final object of this invention that the glove and wrist support be marketable as a kit, or combination, with one of each or two of each, as would be purchased by an individual patent, or a larger number of units as would be appropriate for purchase by a hospital or medical practice.

It should be understood the while the preferred embodiments of the invention are described in some detail herein, the present disclosure is made by way of example only and that variations and changes thereto are possible without departing from the subject matter coming within the scope of the following claims, and a reasonable equivalency thereof, which claims I regard as my invention.

BRIEF DESCRIPTION OF THE DRAWINGS

The following drawings form part of the present specification and are included to further demonstrate certain representative embodiments of the present invention. The invention may be better understood by reference to one or more of these drawings in combination with the detailed description of specific embodiments presented herein.

FIG. 1 is a side, perspective view of an iteration of the splint where it is a wrap-around glove, the splint which highlights the low profile of the splint along with its method of application to a human wrist.

FIG. 2 is a bottom, perspective view of an iteration of the splint where it is a wrap-around glove, showing the method of attaching the splint to the thumb, palm, and digits.

FIG. 3 is a side, perspective view of an iteration of the splint where it is a wrap-around glove with a wrist section for additional support over the iteration shown in FIGS. 1 and 2.

FIG. 4 is a bottom, perspective view of the splint of FIG. 3.

FIG. 5 is a top view of a stay, which can be slid into one of the tunnels or channels on the dorsal side of the splint.

FIG. 6 is top view of an encased stay, where a resilient inner stay, similar to that illustrated by FIG. 5, is encased on one or both sides by a layer of material capable of attachment to other layers of materials, preferably hook and loop fastening material.

FIG. 7 is a top view of a protective wrap, which is a length of cushioning material, preferably neoprene, which is wrapped around the finger on the inside of the digit strap, illustrated by FIG. 8. The protective wrap is soft and pliable, and protects the digit from the sometimes rough texture of the digit strap.

FIG. 8 is a top view of the digit strap, which is a length of material, preferably hook and loop, which is used to wrap around the digit and provide the necessary "pull" to return the digit to an open position following a user's bending of his/her digit. The digit strap can, optionally, wrap over the protective wrap if the user desires to protect his/her digit from the surface of the digit strap. The digit strap has a means of attaching to itself, preferably with hook material on one side and loop material on the other, such that it can be wrapped around the digit and secured onto its own back, but other options, such as snaps are possible.

FIG. 9 is a top view the digit strap laying over the protective wrap.

FIG. 10 is a top view of a resilient digit extensor element, showing the digit strap laying over the protective wrap with the digit strap being wrapped around and secured back onto itself.

Figure 11:
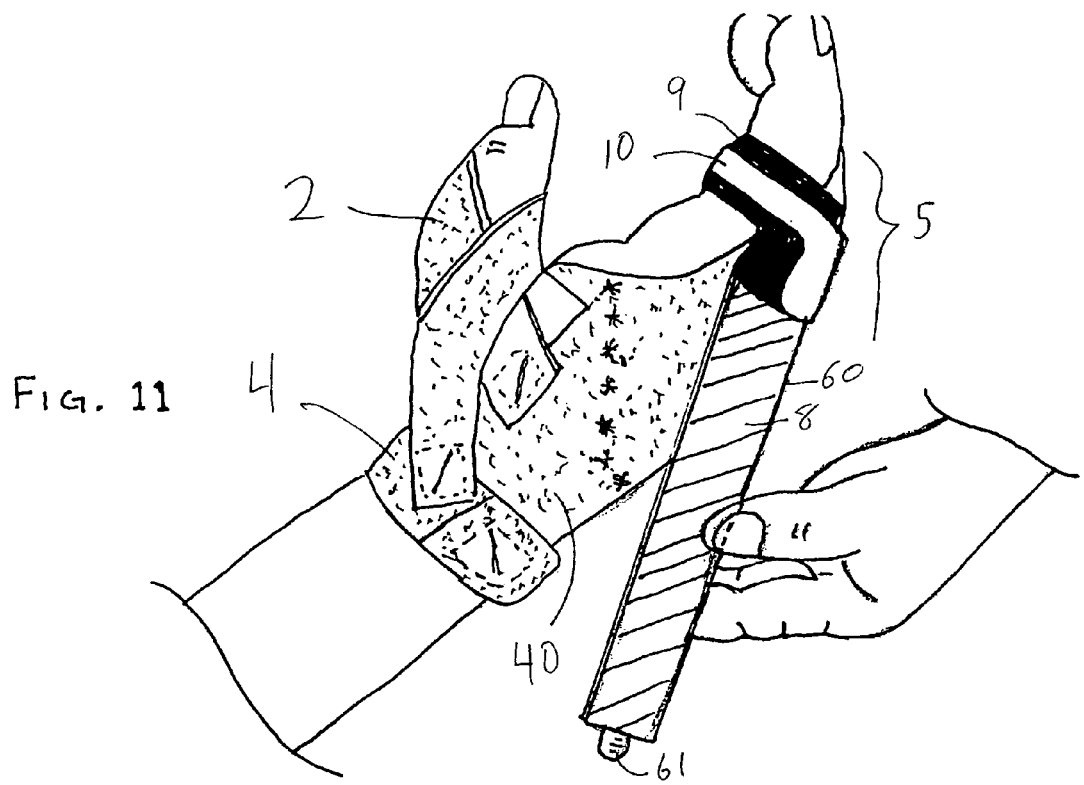
FIG. 11 is a side, perspective view of a resilient digit extensor element, showing the digit strap secured around a digit and being adjustably attached to a glove without wrist support.

It is intended that the drawings of the invention described above are non-limiting and that other features and advantages of the invention will be apparent from the brief description of the drawings, the drawings themselves, the detailed description of the invention, and the appended claims.

DETAILED DESCRIPTION OF THE EMBODIMENTS

The present invention concerns nerve splints for the hand that comprise an orthotic glove. These splints are useful in treating patients having a peripheral neuropathy that results in permanent or temporary full or partial loss of extensor muscle control of one or more digits of a hand. The glove portion of a splint according to the invention provides for customized, patient-specific treatments by including a resilient digit extensor element contained or otherwise disposed in a channel, pouch, or other structure positioned on the dorsal portion of at least a digit section the glove. The extensor element provides sufficient resilience to return the digit to an extended position relaxation of the flexor muscle for that digit. As the amount of tension required to return a particular digit to an extended position will vary between digits and patients, and will even vary over time for the affected digit(s) of a particular patient during the healing process, in preferred embodiments the gloves provide for easy relate to the resilient digit extensor elements. Other features of the splints of the invention relate to their low-profile and aesthetically pleasing nature. Because of their low profile, the splints of the invention may be worn at all times, even while dressing and sleeping.

Turning to the actual shape of the invention, there are several iterations of the invention, but all iterations basically comprise a glove in which the material covering the fingers and thumb on the dorsal and palmer areas of the hand extend over part or all of the digits. In some iterations, one or more of the finger covers are open at the distal end, such that the finger tips of a wearer are exposed when the glove is worn. Such openings can be manufactured to provide exposure of any desired portion of one or more fingers. In a preferred embodiment, the glove material that contacts the skin of the hand and fingers is made of a pliable and resilient material such as neoprene, thermoplastic, thermoplastic covered with cloth or neoprene, cloth, cotton, plastic, leather, or a synthetic material such as neoprene, nylon, or a hypoallergenic material. In certain circumstances where the wearer has extreme sensitivity to touch, the surface of surface of the glove that contacts the skin can comprise neoprene, fur, cotton, or another soft material.

It is also envisioned that the glove can be made from a thermoplastic material, which can be heated to allow the patient or a medical practitioner to heat the glove and bend or otherwise modify it to fit the hand and, optionally, wrist, of the patient. There are several iterations which could successfully use thermoplastic to provide the necessary rigidity to the glove. First, the entire inner core of the glove could be made of thermoplastic material, such that the thermoplastic material would extend to the outer edges of the glove so that the rigid section of the glove would extend around the sides of the hand and, optionally, the wrist. Second, there could be a central core of thermoplastic only in the middle section of the glove, such that there is enough rigidity to support the stays, but there is also a corresponding cost savings in that less of the thermoplastic is used and the glove is less confining. The second version is intended for patients with less severe neural injuries, who do not need any additional wrist support. A variety of other versions are envisioned where the thermoplastic extends further down toward the wrist and out toward the sides of the hands than it does in the second example, but not so far as with the first example.

A key component to the invention is the capability of the glove to accept a stay or resilient digit extensor element, into a tunnel or channel design and manufactured into the dorsal side of the glove. The channel or tunnel substantially tracks that portion of the glove intended for the insertion of a finger. The channel, or in a preferred embodiment, channels—at least one for each finger—are made from a second layer of a material attached or otherwise affixed or removably affixed to the glove material. The second material may be different or the same as the material in contact with the skin. The tunnel or channel material can be attached to the dorsal side of the glove such that one or more tunnels or channels are formed along the dorsal portion of the glove along the back of part of one or more fingers, and, optionally, the thumb. Preferably, the tunnels along the back of the one or more fingers extend the entire length of the finger portions and are sealed with respect to the first material layer on three sides, (i.e., at the leading or distal edges of the finger portions and along each side of the pocket extending from said leading edge to an area near where the wearer's knuckles would rest in the glove, where the tunnel openings are formed). Thus, preferably, the glove has at least four such tunnels and, optionally, five such tunnels, including one for the thumb, along the upper back edge (i.e., along the proximal portion of the wrist) of the glove, extending along the back side of each digit for inserting resilient digit extensor elements. It is also envisioned that the tunnels can be, optionally, made with an adjustable band which encircles the digit, such that the same tunnel can be used with any finger or thumb in an interchangeable manner.

The channels are designed and manufactured for insertion and removal of resilient digit extensor elements, or stays, that compensate for loss of digit extensor function. In preferred embodiments, the gloves allow for removal and replacement of the resilient digit extensor elements as the needs of the patient change over time. The resilient digit extensor elements are typically elongate strips made of a synthetic material having memory or spring-like qualities. In some embodiments, the resilient digit extensor elements are planar and linear and of a length specific for the size of the glove and the channel into which the element is e inserted or otherwise positioned in the glove. In preferred embodiments in which the gloves are configured to accept two or more resilient digit extensor elements, the resilient digit extensor elements used for a particular have different degrees of resilience matched to the strength or weakness of finger muscles of the wearer.

The glove works by providing a mechanisms and means for applying adjustable and controlled amounts of extensor tension to the patient's fingers so that an appropriate level of resistance can be set for an individual patient, thereby allowing the wearer to realize full flexor capability while keeping the fingers in a neutral, relaxed position when not flexed in an extended an relaxed posture. Another iteration of the invention concerns a larger orthotic glove into which a patient's hand fits (as opposed to the "wrap around" version which uses straps to attach the patient's fingers, palm and wrist to the device) operably connected to wrist support that provides for wrist extension.

The glove also can, optionally, have a number of different versions with respect to wrist support. It is envisioned that a basic glove would extend from the mid-digital area to the area of the wrist. For patients requiring some wrist support as well, an additional iteration is discussed which provides wrist support. This wrist support can be provided in one of two ways: a glove which extends from the mid-digital area down to the dorsal forearm, and the basic glove with a wrist support add-on which can be inserted into a receptacle in the basic glove and thereby be affixed to the basic glove.

The invention, in all its iterations, provides a device and method for the treatment of radial and peripheral nerve injuries. The invention provides methods of compensating for full or partial, permanent or temporary loss of extensor function of one or more digits of a patient suffering from a radial or peripheral neuropathy. In addition to protecting the injured hand, the invention allows for a medical practitioner to customize treatments for individual patients by selecting particular resilient digit extensor elements for each affected digit.

Also, over time and as a patient's condition improves or worsens, some or all of the various resilient digit extensor elements may be exchanged for other resilient digit extensor elements having differing levels of resilience depending upon the success or failure of the wearer to increase voluntary control of the flexor and/or extensor muscles for each individual digit. It is also anticipated that the variations in the glove—namely, whether it contains wrist support, what kind of wrist support is supplied, and whether the glove is made rigid and if so, with how much rigidity—will also allow some convenient flexibility in treatment plans.

The figures, while not limiting the invention to any one or several particular iterations, are design to provide an illustrative view of several of the most promising iterations.

FIG. 1 is a side, perspective view of an iteration of the splint where it is a wrap-around glove, the splint which highlights the low profile of the splint along with its method of application to a human wrist. The glove has a dorsal side (1) which fits over the dorsal metacarpal portion of a user's hand. Rather than having a solid bottom or palmar side, as will be seen in additional iterations of the invention, this iteration has straps that wrap around the user's wrist/hand had to secure the dorsal side (1) to the user's hand and wrist. There is a palmar or wrist retention strap (4) which secures the glove to the hand, a thumb retention strap that secure the glove to the thumb, and resilient digit extensor elements (5) that restrain the fingers against the stays (8). The resilient digit extensor elements (5) are comprised of three basic components: a stay (8) which is a resilient, narrow, band of metal, fiberglass, plastic or some other inexpensive, easy to manufacture, and easy to use material, a protective wrap (9), which is a comfortable band of material, for example, neoprene, that cushions and protects the digit from the digit strap (10), which is a sturdy strip of material with means, preferably hook and loop, to fasten it onto its own back after being wrapped around a digit. As such, each resilient digit extensor element can be adjusted so that the glove fits a wide range of hand sizes and shapes, and so that a user can customize the fit for the user's comfort. It is envisioned that one method of accomplishing having the resilient digit extensor elements (5), the wrist retention strap (4), and the thumb retention strap (2) would be to have a small tab of hook or loop (12) located on the distal end of each such strap, with a corresponding patch of the mating surface (either hook or loop) located where it is anticipated that the distal end would attach. Another iteration involves making each strap with one side hook and the other loop, such that attachment can be accomplished merely by looping the strap around and back upon itself. An additional iteration involves making the surface of the glove with one texture (hook), and make the sections of all straps that will attach to the glove of the opposite texture (loop). It is envisioned that this iteration, along with the others described in this application, can be made in a wide variety of colors, including skin colors such that the glove will blend in with a person's skin and not be obvious.

FIG. 2 is a bottom, perspective view of an iteration of the splint where it is a wrap-around glove, showing the method of attaching the splint to the thumb, palm, and digits. The wrist retention strap (4) is a band of material, preferably a thin yet sturdy material, with, optionally, a degree of elasticity. The wrist retention strap (4) serves to anchor the glove to the wrist, thereby avoiding the possibility that the glove would "run up" the user's hand. The thumb retention strap (2), wraps around the user's thumb and then is pulled down and laterally across the bottom side of the user's thumb, and secured to the outer surface of the wrist retention strap (4) on a portion of the wrist retention strap (4) that has a section of hook and loop, snaps, or other means of attachment on a location on the wrist retention strap (4) that is optimally located to receive a mating section of hook and loop, snaps, or other means of attachment on the distal end of the thumb retention strap. Connecting the wrist, thumb and finger portions of the invention is a palm section (14), which can be made from a variety of materials, including but not limited to suede, neoprene, or any other comfortable and durable material. The resilient digit extensor elements (5) in this figure also have a quick-release tab (11) which can be used to quickly detach or adjust the resilient digit extensor elements. As can be seen from FIGS. 1 and 2, with the three points of retention, wrist, palm and fingers, a stay put in the backside of the glove will hold "open" the fingers, as is necessary for not only the protection and treatment of damage to the peripheral or radial nerves, but also to allow the user to effectively grip objects and have his/her hand move back to an "open" position from which he/she can grip additional objects once the user releases the first object. FIGS. 1 and 2 show the user's hand in an "open position".

FIG. 3 is a side, perspective view of an iteration of the splint where it is a wrap-around glove with a wrist section for additional support over the iteration shown in FIGS. 1 and 2. This is basically similar to the glove illustrated by FIGS. 1 and 2, except that this iteration provides additional wrist support in the form or a wrist extension (22) with a forearm band (20) including a forearm retention strap (21) that is designed similar to the wrist retention strap (4) and provides a similar purpose. The wrist extension (22) can be made from elastic material, thermoplastic or other moldable and/or adjustable materials, fiberglass or other non-adjustable materials, or other material which will give the splint the amount of rigidity needed. Item 23 is, in this figure, the user's skin, but it is envisioned that there would be a need for a wrist support which extended all the way around the wrist and forearm of the user, such that additional iterations of the invention will have a solid, supportive material covering the user's skin.

FIG. 4 is a bottom, perspective view of the splint of FIG. 3, showing how the forearm band (20) encircles the forearm and provides additional wrist support. This figure also illustrated how the wrist retention strap (24) can be designed to appear to be much more of a fluid continuation of the glove rather than a band of material that was obviously sewn on with little concern for appearances (see (4) in FIGS. 1, 2, and 3).

FIG. 5 is a top view of a stay (30), which can be slid into one of the tunnels or channels on the dorsal side of the splint. The stay is a resilient piece of metal, plastic, fiberglass, or some other material that is semi-rigid and resilient. The width, thickness, and material from which it is comprised determines the rigidity of the stay. Since different patients with different gloves require different stays, and, indeed, during the treatment regimen many patients will need stronger or weaker stays as treatment progresses, the view shown here is not intended to be limiting as to variety of stays envisioned. The stay here is shaped like a popsicle stick, but it is envisioned that a variety of shapes and sizes of stays can be used, depending on the patient needs and the design of the glove. This stay is used in the iteration of the invention which has tunnels, or channels, which are hollow tubes of material sewn onto the dorsal side of the invention, described more fully in related application Ser. No. 11/145,777, which is a continuation of application No. 60/641,205. An alternative method of allowing a person with radial nerve damage or some other medical condition preventing him/her from opening the hand once it is closed is illustrate by FIGS. 6-10.

FIG. 6 is top view of an encased stay, where a resilient inner stay (61), similar to that illustrated by FIG. 5, is encased on one or both sides by a layer (60) of material capable of attachment to other layers of materials, preferably hook and loop fastening material.

FIG. 7 is a top view of a protective wrap (9), which is a length of cushioning material, preferably neoprene, which is wrapped around the finger on the inside of the digit strap, illustrated by FIG. 8. The protective wrap is soft and pliable, and protects the digit from the sometimes rough texture of the digit strap. The protective wrap has a finger portion (9B), and an attachment portion (9A) which attaches the protective wrap to the encased stay (not shown in this figure). The protective wrap can be made, optionally, of one side or two sides, of hook and loop or some other material which can be used to attach the protective wrap to the encased stay and to the digit strap (illustrated in FIG. 8).

FIG. 8 is a top view of the digit strap (10), which is a length of material, preferably hook and loop, which is used to wrap around the digit and provide the necessary "pull" to return the digit to an open position following a user's bending of his/her digit. The digit strap can, optionally, wrap over the protective wrap (from FIG. 7) if the user desires to protect his/her digit from the surface of the digit strap. The digit strap has a means of attaching to itself, preferably with hook material on one side and loop material on the other, such that it can be wrapped around the digit and secured onto its own back, but other options, such as snaps are possible. The protective wrap has a finger portion (10B), and an attachment portion (10A) which attaches the protective wrap to the encased stay (not shown in this figure).

FIG. 9 is a top, partial cut-away view the digit strap (10) laying over the protective wrap (9), with the encased stay (60) in the middle. The stay (62) has been slid into the encasing structure (63), such that just its distal end (61) is visible. The distal end (61) is used to remove the stay (62) from the encasing structure (63) when it is desirable to do so. For example, should the patient begin to regain use of his/her hand functions, it is possible the a weaker stay would be inserted to force the patient to work harder at opening up his/her hand after closing it. The resilient digit extensor elements are comprised of three basic components: a stay which is a resilient, narrow, band of metal, fiberglass, plastic or some other inexpensive, easy to manufacture, and easy to use material (the tip of which is seen as item 61), a protective wrap (9), which is a comfortable band of material, for example, neoprene, that cushions and protects the digit from the digit strap (10), which is a sturdy strip of material with means, preferably hook and loop, to fasten it onto its own back after being wrapped around a digit. As such, each resilient digit extensor element can be adjusted so that the glove fits a wide range of hand sizes and shapes, and so that a user can customize the fit for the user's comfort.

FIG. 10 is a top view of the resilient digit extensor element, showing a digit strap (10) laying over the protective wrap (9) with the digit strap being wrapped around and secured back onto itself (64). Here, a user can use one hand to completely secure the digit strap (10) around a digit, and thereby secure the invention to his/her hand without requiting another person to assist.

FIG. 11 is a side, perspective view of a resilient digit extensor element, showing a digit strap (10) secured around a digit and being adjustably attached to a glove without wrist support. This figure illustrates how a digit strap (10) can be wrapped around a digit, with an optional protective wrap (9) placed in between the digit and the digital strap. The digital strap and protective wrap are connected to an encased stay (generally referred to by reference number 8). The encased stay has an encasing structure (60) into which a stay (visible here only at its distal end (61) is inserted. The encasing structure has a surface which can be attached to the dorsal surface (40) of the glove, preferably by hook and loop fasteners. The hook and loop allow the user of the invention to easily and quickly secure the resilient digit extensor around a digit and then attach it to the glove, as well as providing substantial adjustability, as the resilient digit extensors can be attached anywhere on the dorsal surface (40) of the glove where there is the mating side of hook and loop as it contained on the bottom side of the encased stay (8).

Figure 12:
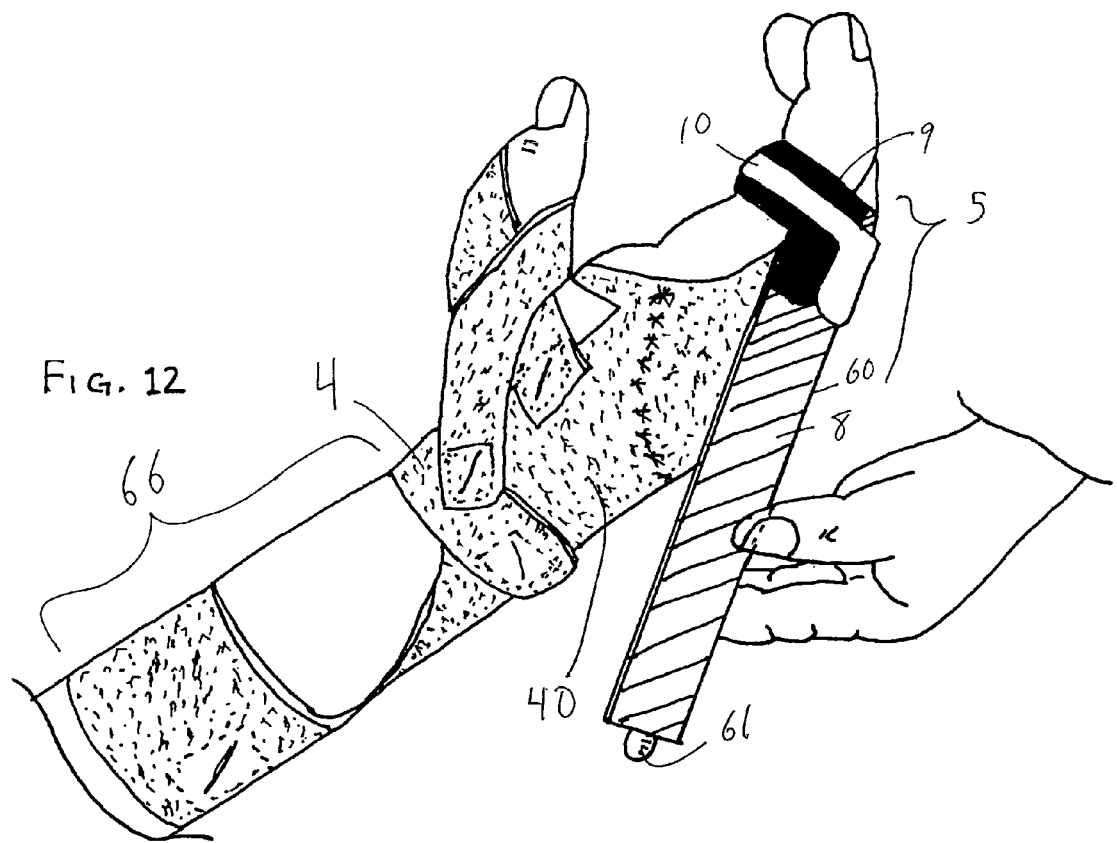
FIG. 12 is a side, perspective view of a resilient digit extensor element, showing the digit strap secured around a digit and being adjustably attached to a glove with wrist support.

FIG. 12 is a side, perspective view of a resilient digit extensor, showing a digit strap (10) secured around a digit and being adjustably attached to a glove with wrist support (66).

Figure 13:
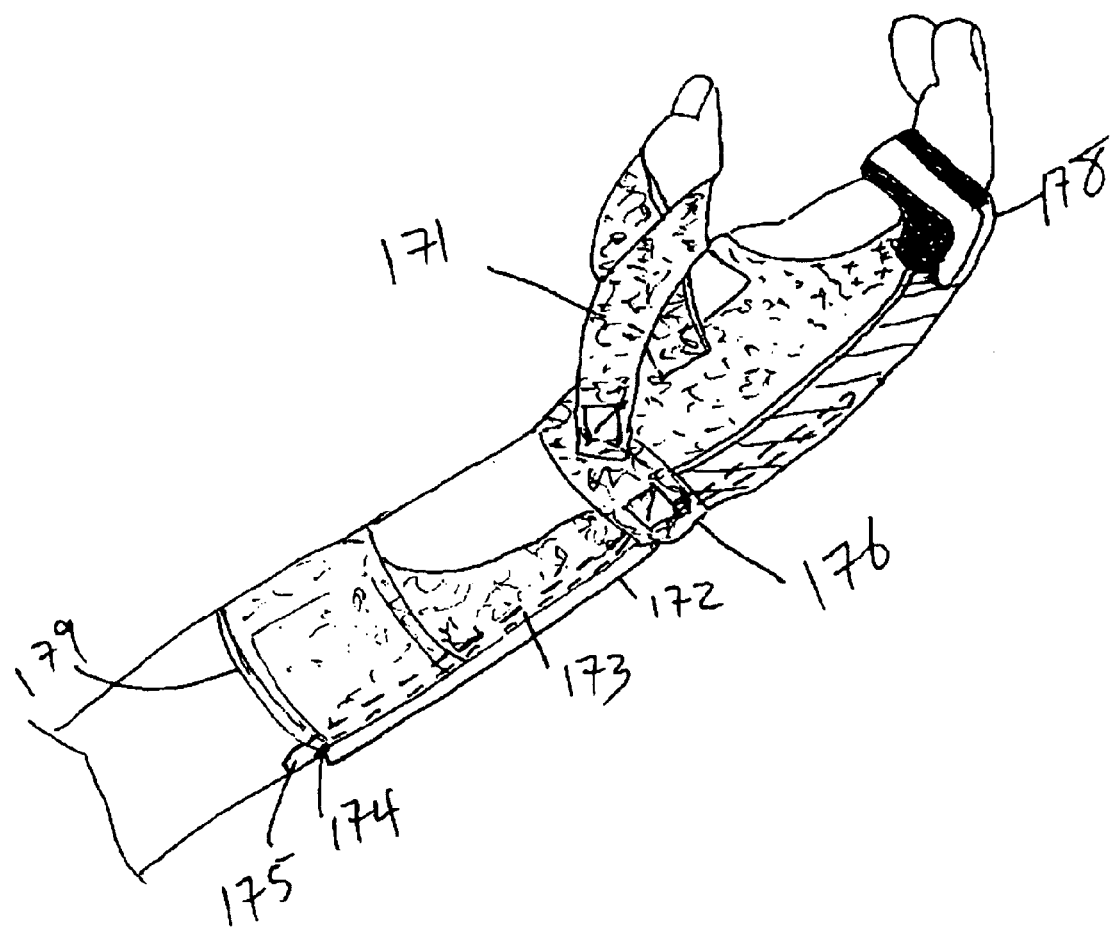
FIG. 13 is a perspective side view of the glove with a removable wrist stay in a sleeve built into the dorsal side of the glove.
Figure 17:
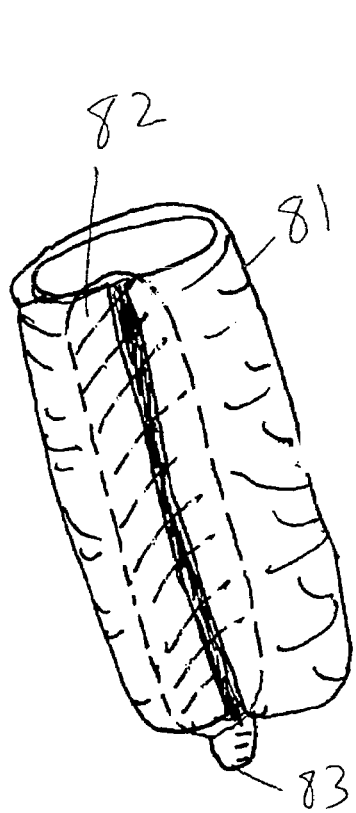
Figure 18:
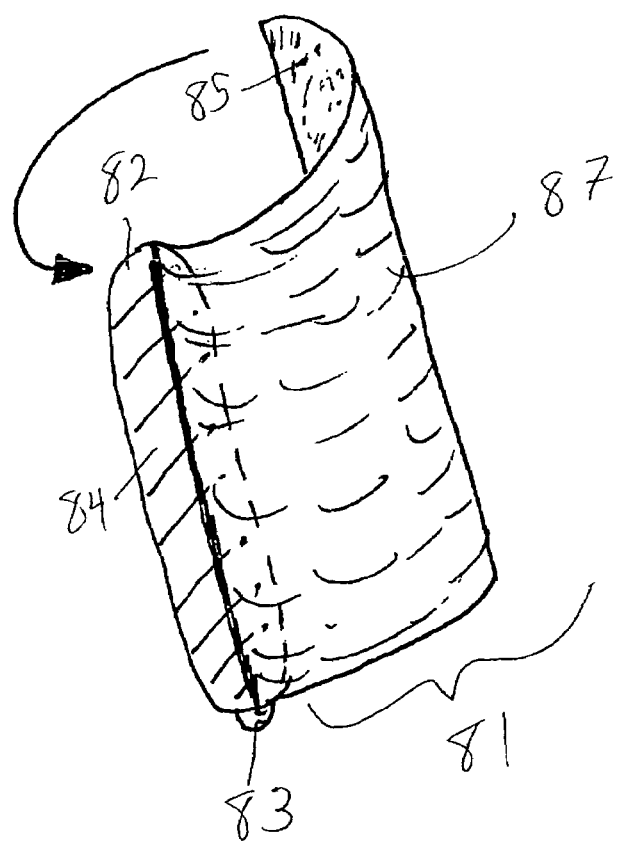
Figure 19:
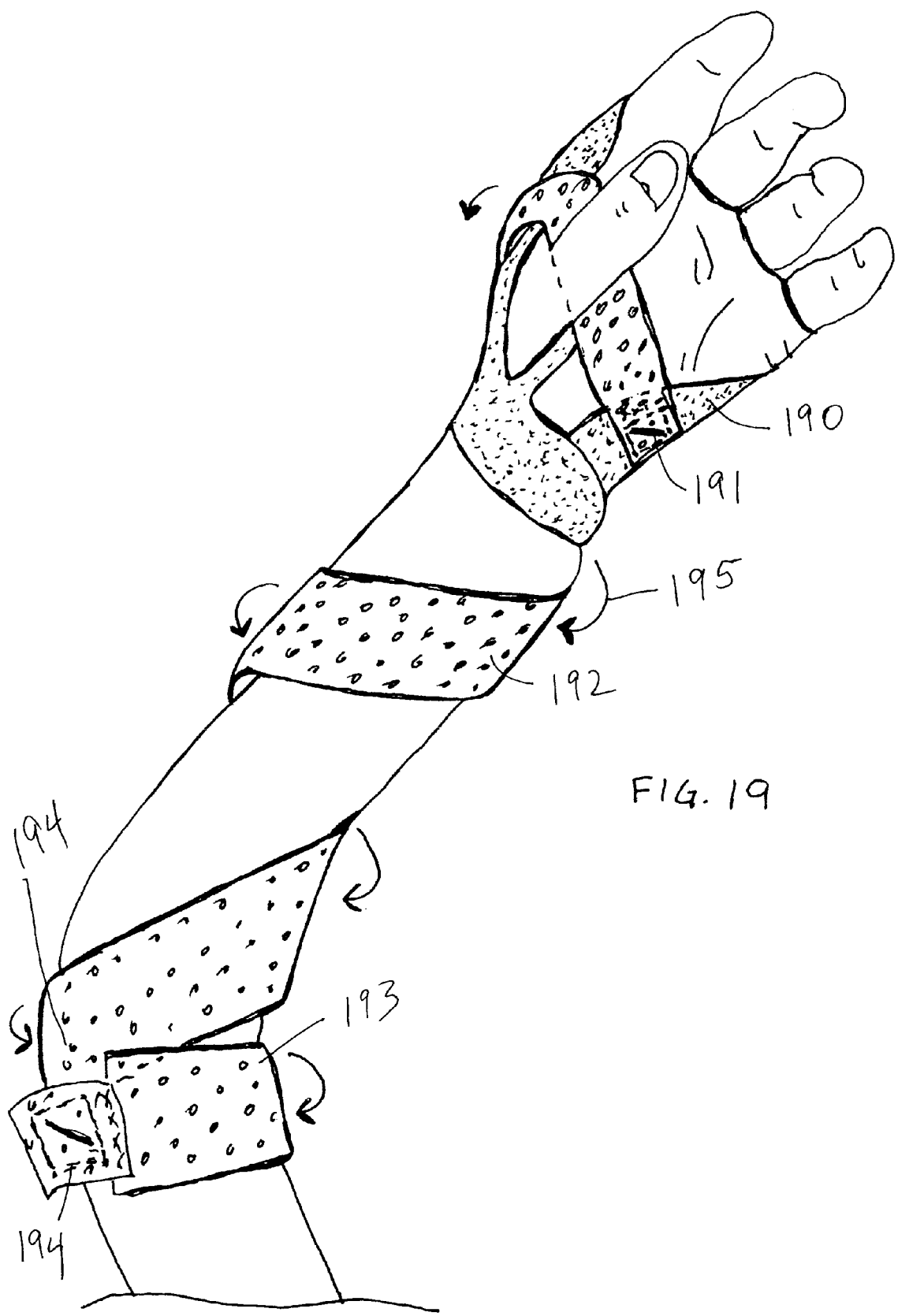

FIG. 13 is a perspective side view of the glove with a removable wrist stay in a sleeve built into the dorsal side of the glove. In this version, the glove, generally reference by number 171, has a wrist stay channel 172 that extends from the end of the glove 179 closest to the user's elbow, to proximate to the end of the glove 178 closest to the person's fingers. Into this wrist stay channel 172, a stay 173 in inserted. The stay can be inserted through an opening 174 at the elbow end 179 of the glove, or through a hole located somewhere in the middle of the channel, as described in more detail in related application Ser. No. 11/145,777, FIG. 17. With the version illustrated here, the stay 173 can be adjustably inserted such that a portion 175 can extend out the opening 174. To further secure the stay 173, the wrist wrap 176 can be tightened over the stay. Through the wrist stay channel extending from one side of the user's wrist to the other, the wrist can be adjustably supported and partially immobilized if that is desirable as part of the treatment.

Figure 14:
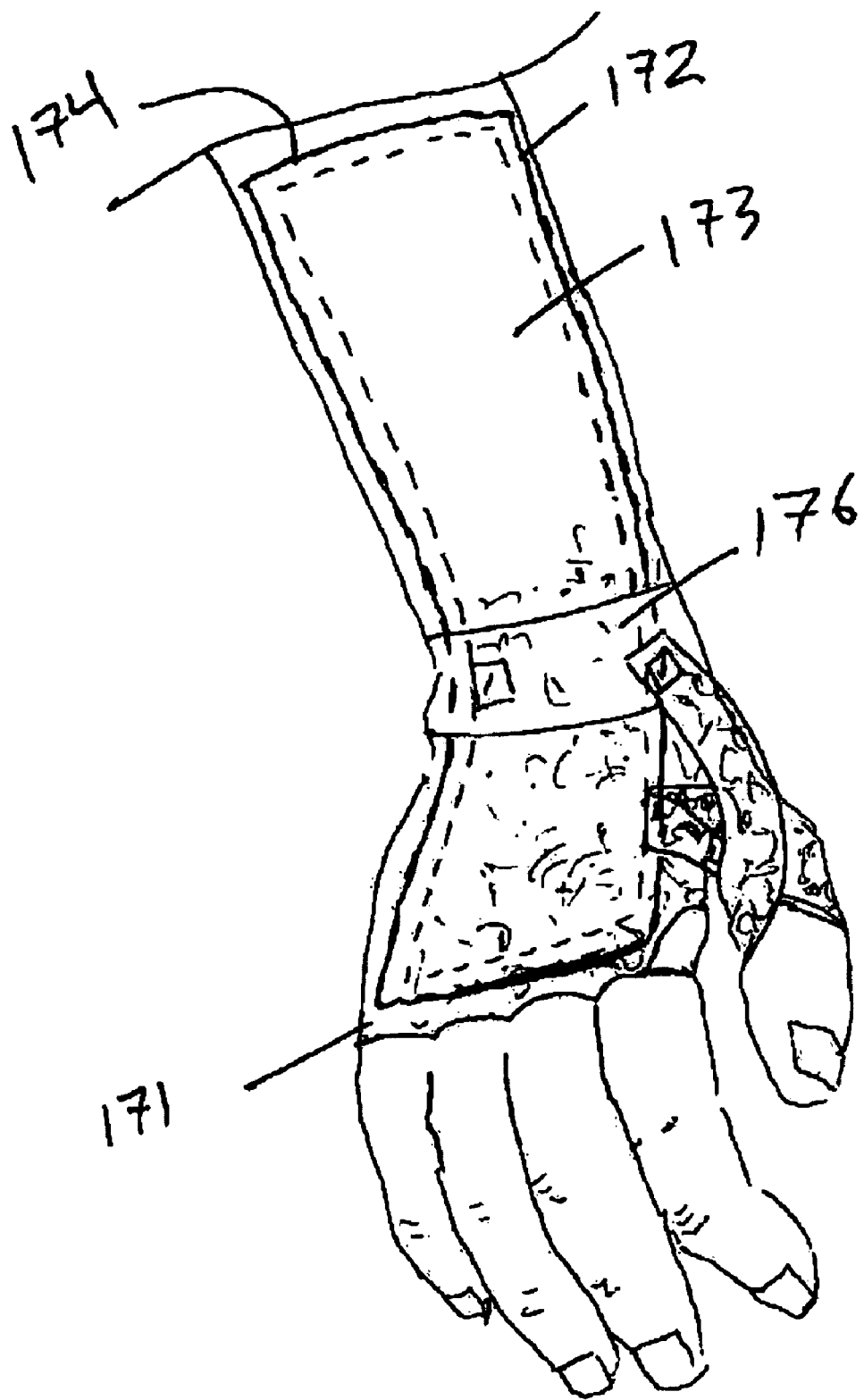
FIG. 14 is a top view of the glove with a removable wrist stay in a sleeve built into the dorsal side of the glove.

FIG. 14 is a top view of the glove with a removable wrist stay in a sleeve built into the dorsal side of the glove. In this figure, the wrist stay 173 is inserted into the wrist stay channel 172 through the opening 174.

Figure 15:
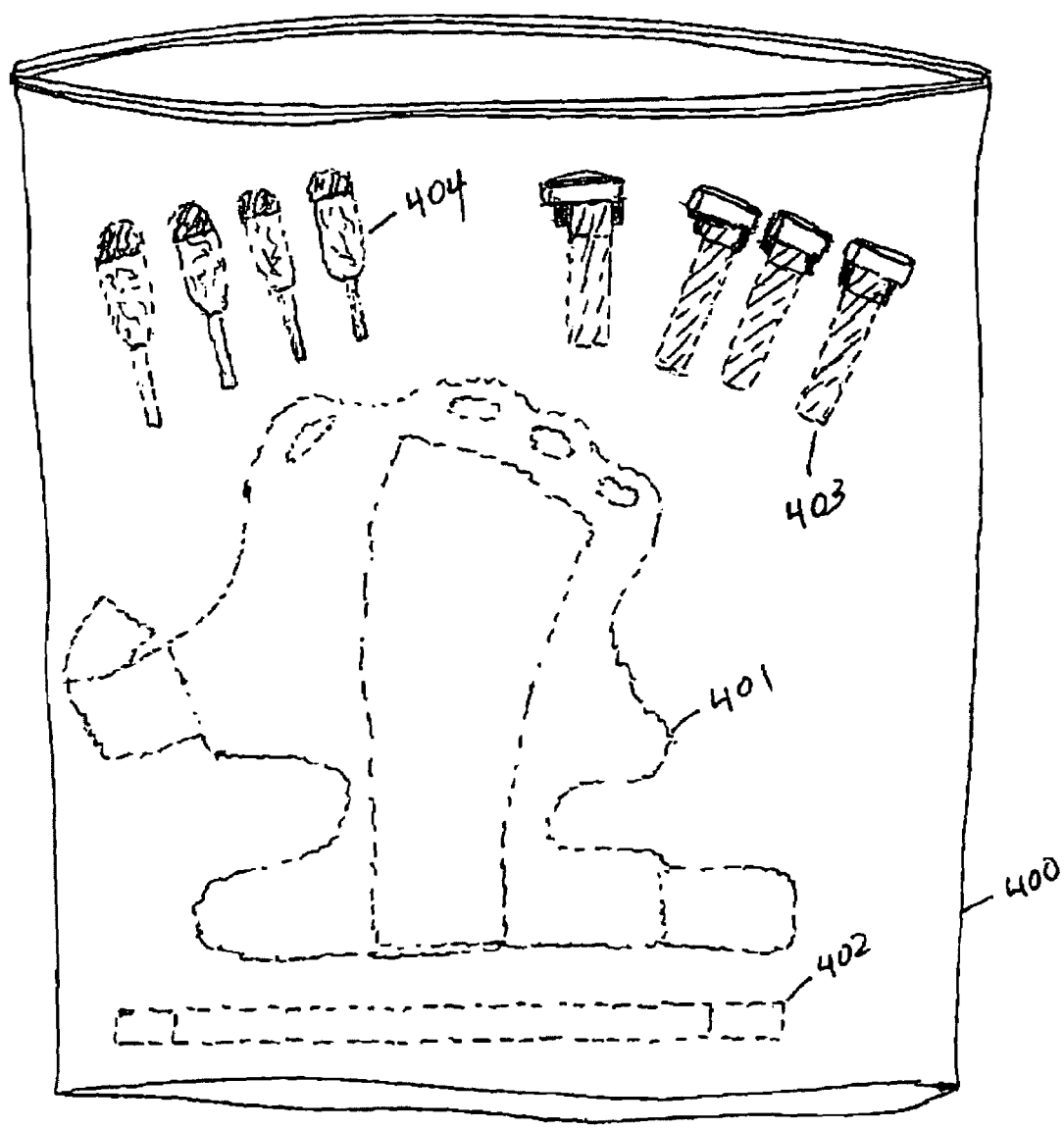
FIG. 15 is a top view of a retail package for the invention showing how it could be displayed.
Figure 16:
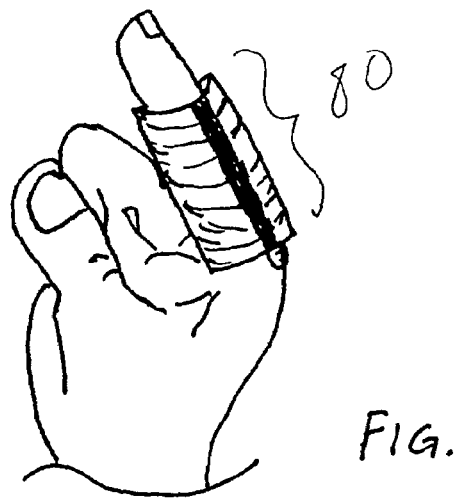

FIG. 15 is a top view of a retail package for the invention showing how it could be displayed. The package 400 is preferably a clear, plastic "blisterpack" which clearly shows the glove 401, the stays 402, the resilient digit extensor elements 403, and the fingertip retaining extensor elements 404.

As those in the art will appreciate, the hand splints of the invention have a substantially flat or "low" profile due to the thin nature of the materials and components used in the glove portion. The low profile enhances the aesthetic quality of the glove, in that the splint is much less visible to others when worn, and in any event appears very much like conventional weight-lifting, sailing, or other sports gloves or fashion accessories. In addition, the low profile nature of the splint allows the wearer to easily wear the glove while conducting normal or routine activities such as in dressing, bathing, and eating.

Further still, in yet another embodiment, the invention provides for a treatment regimen wherein one or more of a first set of extensor elements are exchanged over time with extensor elements having a greater or lesser the degree of resilience and/or curvature depending upon the progress being attained with the then-current one or more resilient digit extensor elements.

In still other embodiments, the splint can be used to treat various neuropathy disorders, including those that affect both the ability to extend the digits or wrist and the ability to flex the digits. Similarly, the splints of the splints of the invention can also be used by healthy subjects, for example, to increase grip strength (by overcoming resistance to flexion of digit flexor muscle). An embodiment useful for therapy is described in the following example.

Where a patient has suffered a nerve or muscle injury that affects the ability of the patient to extend at least one digit of a hand, a glove according to the invention may be placed on the hand to effect treatment. The patient often has difficulties/inabilities to extend his/her wrist secondary to neurological dysfunction or paralysis, thereby requiring permanent or temporary wrist support. Preferably the patient is first tested by his/her attending physician, physical/occupational therapist, or other rehabilitation provider to determine the extent of the nerve and/or muscle deficit with respect to the digit(s) involved. Depending upon the ability or inability to extend or flex the at least one digit, a resilient digit extensor element of appropriate resilience and design is inserted between the pockets of the glove that are designed to effect therapy for the particular digit. The patient is then instructed to wear the splint as necessary or according to an exercise/treatment protocol.

If, during the course of therapy, the patient achieves sufficient progress (or not), a determination may be made to exchange one or more of the resilient digit extensor elements for others have differing degrees of resilience in order to further advance therapy.

As will be apparent to those of ordinary skill in the art in the light of the foregoing disclosure, many alterations and modification are possible in the practice of this invention without departing from the spirit or scope thereof. Accordingly, the scope of the invention is to be constructed in accordance with the substance defined by the following claims.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

What I claim as my invention is:

1. An orthotic splint for treating radial or peripheral nerve damage, comprising:
    a dorsal metacarpal element, where the dorsal metacarpal element covers at least a portion of a user's hand,
    a ventral palmar element, where the ventral palmar element covers less than a majority of the user's palm,
    a flexible thumb strap that keeps the thumb properly positioned, where the thumb strap is easy to secure and comfortable to the user,
    a means of attachment by which the dorsal metacarpal element and the ventral palmer element are attached to each other,
    at least one resilient digit extensor extending from the dorsal metacarpal element past the Metacarpophalangeal joint and stopping before the distal interphalangeal joint,
    at least one encasing structure or channel capable of accepting a stay, where each encasing structure comprises a top, a bottom, a closed end and an open end, where the top and bottom are attached to each other on the sides and on the bottom of the top and bottom sections, such that the encasing structure functions as a closed-ended channel into which the stay can be inserted, where the at least one resilient digit extensor comprises the combination of an encasing structure and a stay, and where the at least one resilient digit extensor is removably attached to the orthotic splint, and where the at least one resilient digit extensor has a means of attachment to the dorsal metacarpal section, and where the means of attachment is hook and loop fasteners in the form of mated pairs of hook and loop fasteners, and where the at least one resilient digit extensor is adjusted by removing it from the orthotic splint and reattaching it to a different location on the orthotic splint, such that a medical practitioner can adjust the angle and position of each resilient digit extensor to correct for problems common to recovering radial nerve injuries such as bent fingers and nerves that recover in irregular patterns causing irregular control by a patient of his/her fingers, where the mated pairs of hook and loop fasteners comprises one section hook fastener and one section of loop fastener, and where the one section of hook fastener and the one section of loop fastener can be removably attached to each other, where, the splint functions by keeping the patient's hand in an "open" position, such that the flexor muscles can close the hand to grasp objects and perform many daily, routine activities, and that the resilient digit extensors of the splint will then push the fingers and thumb of the hand back into the "open" position once the grasping action is no longer desired, and, where the splint has no outriggers, loops, wires, or other projections sticking out of it more than ¼ inch above the surface of the glove, where the exposed skin on a user's hand and at least one digit provides the user of the invention with tactile sensation and direct sensory feedback, thereby allowing the user to easily feel and grasp objects in the user's hand as well as to recover faster from a radial never injury, as the direct contact between the ventral portion of the user's hand allows the user and a medical professional overseeing the user's treatment to determine progress in the user's ability to grasp various objects and modify the splint to accelerate the user's recovery.

2. The splint of claim 1, additionally comprising a means of adjustment by which the splint is adjusted to an individual user's hand size, where the means of adjustment is the natural elasticity of the glove material, adjustable straps, adjustable zippers, adjustable snaps, Hook and loop fastener, threaded string or similar devices, and, a means of securing the glove to the user's hand, where the glove is designed such that it is easily and conveniently put on and taken off, and, where, the splint is made in a variety of sizes to accommodate the different sizes of hands, where, the splint is manufactured from a material, selected from a group comprising: plastic, leather, lycra, polyester, imitation leather, neoprene, and compression garment material, where the splint is made for the right hand or the left hand, and, where the splint is of a low profile such that no portion of the glove extends above the palm or dorsal portions of the hand by more than ½ inch, such that it is worn during many daily activities such that a patient is likely to use the splint outside of the medical practitioner's office, and, where the material from which the splint is made can, optionally, be of a skin color or other color designed to make the splint unobvious when being worn.

3. The splint of claim 1, where the splint additionally comprises at least one resilient digit extensor element that extends toward the end of a user's finger to at most the Proximal interphalangeal joint (PIP joint).

4. The splint of claim 1, where each stay has an independently selected resilience such that a user or medical practitioner can select stays of different resistances for different fingers depending on different neural and muscle strengths and different treatment regimes, and can exchange individual stays as a patient's treatment progresses and the patient's condition changes.

5. The splint of claim 1, where the stay comprises a resilient material from the group consisting of a synthetic carbon-based plastic, rubber, polyethylene, polycarbonate, polyvinyl chloride, a metal, a metal alloy, and a combination of any two or more of the foregoing materials.

6. The splint of claim 1, where the stay has two ends and is tapered such that one end is thicker than the other end, and, where said stay element has less resilience at a thin end than at a thick end.

7. The splint of claim 1, where the at least one encasing structure or channel capable of accepting a stay additionally comprises a top, a bottom, and two closed ends and two closed sides, where the top and bottom are attached to each other on the two closed sides and the two closed ends, such that the encasing structure functions as a closed channel into which the stay is permanently inserted.

8. The splint of claim 1, where the splint allows for use by patients with less than a 15 pound grip.

9. The splint of claim 1, where the splint allows for use by patients with less than a 25 pound grip.

10. The splint of claim 1, where the means of attachment between the dorsal metacarpal element and the at least one resilient digit extensor allows a resilient digit extensor to be substituted for another easily and quickly.

11. The splint of claim 1, where each channel has a terminal end and an encircling element comprising a flat section of material attached at one end to the terminal end of the digit extensor element, a central section of material long enough to wrap around a digit of a person, and end, and means of securing the end to the encircling element.

12. The splint of claim 1, where at least two resilient digit extensors have at least two stays of different tensile strength, such that a medical practitioner can replace an existing resilient digit extensor with another of a different tensile strength depending on the progress of the patient.

13. The splint of claim 1, where the glove additionally comprises a quantity of thermoplastic.

14. The splint of claim 13, where the thermoplastic extends from the dorsal forearm to the top of the hand.

15. The splint of claim 13, where the thermoplastic extends from above the wrist to the top of the hand.

16. The splint of claim 13, where the thermoplastic extends from above the wrist to the top of the hand and does not extend down the dorsal forearm and does not extend beyond the top of the hand.

17. The splint of claim 1, where the splint additionally comprises a wrist support device, where the wrist support device comprises a wrist stay base channel, a wrist stay of a length such that the wrist stay is partially inserted into the wrist stay base channel so that an appropriate length of the wrist stay extends out of the opening of the wrist stay base channel and is inserted into a wrist stay receptacle of the splint, and, one or more lengths or bands, consisting of a length of flexible material, optionally with some elasticity and means of adjustment and attachment to allow a user to snugly and comfortably fit the wrist support device to his/her wrist, where, by inserting the wrist stay into the wrist stay receptacle on the splint, the user is operably connect the wrist stay and the splint.

18. A method for treatment of a full or partial loss of extensor function for one or more digits of a hand, the method comprising placing an orthotic splint on a hand of a subject who suffers from full or partial loss of extensor function for one or more digits of the hand, thereby compensating for full or partial loss of extensor function for one or more digits of the hand, where such splint comprises:

- a dorsal metacarpal element, where the dorsal metacarpal element covers at least a portion of a user's palm, but less than a majority of the user's palm,
- a ventral palmar element, where the ventral palmar element covers at least a portion of a user's hand,
- a flexible thumb strap that keeps the thumb properly positioned, where the thumb strap is easy to secure and comfortable to the user,
- a means of attachment by which the dorsal metacarpal element and the ventral palmer element are attached to each other,
- at least one digit section extending from the dorsal metacarpal element and palmar element past the Metacarpophalangeal joint,
- at least one channel capable of accepting a resilient digit extensor element, where each channel spans from the dorsal metacarpal element to a dorsal area of a digit section,
- at least one resilient digit extensor element in a channel, and, where, the splint functions by keeping the patient's hand in an "open" position, such that the flexor muscles can close the hand to grasp objects and perform many daily, routine activities, and that the resilient digit extensor elements of the splint will then push the fingers and thumb of the hand back into the "open" position once the grasping action is no longer desired, and, where the splint has no outriggers, loops, wires, or other projections sticking out of it more than ¼ inch above the surface of the glove, and, where the splint additionally comprises a quantity of thermoplastic where the exposed skin on a user's hand and at least one digit provides the user of the invention with tactile sensation and direct sensory feedback, thereby allowing the user to easily feel and grasp objects in the user's hand as well as to recover faster from a radial never injury, as the direct contact between the ventral portion of the user's hand allows the user and a medical professional overseeing the user's treatment to determine progress in the user's ability to grasp various objects and modify the splint to accelerate the user's recovery.

* * * * *